(12) United States Patent
Chen

(10) Patent No.: US 7,883,524 B2
(45) Date of Patent: Feb. 8, 2011

(54) METHOD OF DELIVERING AN INTRAGASTRIC DEVICE FOR TREATING OBESITY

(75) Inventor: Steve Kaipin Chen, Carmel, IN (US)

(73) Assignee: Wilson-Cook Medical Inc., Winston-Salem, NC (US)

(*) Notice: Subject to any disclaimer, the term of this patent is extended or adjusted under 35 U.S.C. 154(b) by 397 days.

(21) Appl. No.: 11/963,577

(22) Filed: Dec. 21, 2007

(65) Prior Publication Data
US 2009/0164028 A1    Jun. 25, 2009

(51) Int. Cl.
*A61M 29/00* (2006.01)

(52) U.S. Cl. ................... 606/191; 623/23.65

(58) Field of Classification Search ........ 623/23.64–68, 623/191–200, 1.11, 1.23; 606/191–200
See application file for complete search history.

(56) References Cited

U.S. PATENT DOCUMENTS

| | | | |
|---|---|---|---|
| 2,508,690 A | 5/1950 | Schmerl |
| 4,133,315 A | 1/1979 | Berman et al. |
| 4,134,405 A | 1/1979 | Smit |
| 4,246,893 A | 1/1981 | Berson |
| 4,315,509 A | 2/1982 | Smit |
| 4,403,604 A | 9/1983 | Wilkinson et al. |
| 4,416,267 A | 11/1983 | Garren et al. |
| 4,485,805 A | 12/1984 | Foster, Jr. |
| 4,558,699 A | 12/1985 | Bashour |
| 4,607,618 A | 8/1986 | Angelchik |
| 4,694,827 A | 9/1987 | Weiner et al. |
| 4,696,288 A | 9/1987 | Kuzmak et al. |
| 4,723,547 A | 2/1988 | Kullas et al. |
| 4,803,985 A | 2/1989 | Hill |
| 4,878,905 A | 11/1989 | Blass |
| 4,899,747 A | 2/1990 | Garren et al. |
| 4,925,446 A | 5/1990 | Garay et al. |
| 4,952,339 A | 8/1990 | Temus et al. |
| 5,129,915 A | 7/1992 | Cantenys |
| 5,234,454 A | 8/1993 | Bangs |
| 5,246,456 A | 9/1993 | Wilkinson |
| 5,306,300 A | 4/1994 | Berry |
| 5,327,914 A | 7/1994 | Shlain |

(Continued)

FOREIGN PATENT DOCUMENTS

EP    0137 878    11/1983

(Continued)

*Primary Examiner*—Todd E Manahan
*Assistant Examiner*—Christopher Schubert
(74) *Attorney, Agent, or Firm*—Brinks Hofer Gilson & Lione

(57) ABSTRACT

An intragastric member and method of delivery thereof are described. Delivery of the intragastric member is enabled by partitioning the intragastric member into discrete bundles with retaining members that are circumferentially disposed along the longitudinal length of the intragastric member. Formation of the intragastric member into bundles facilitates controlled delivery into the gastric lumen. The use of suture ties enables deployment of the intragastric member into the gastric lumen. The distal ends of the suture ties are affixed to the bundles. Pulling on the proximal free end of each of the suture ties enables the corresponding bundles to be advanced distally along a delivery tube. The suture ties are pulled until each of the bundles slide off from the delivery tube and enter into the gastric lumen.

14 Claims, 10 Drawing Sheets

U.S. PATENT DOCUMENTS

| | | | |
|---|---|---|---|
| 5,345,949 A | 9/1994 | Shlain | |
| 5,868,141 A | 2/1999 | Ellias | |
| 5,938,669 A | 8/1999 | Klaiber et al. | |
| 5,993,473 A | 11/1999 | Chan et al. | |
| 6,067,991 A | 5/2000 | Forsell | |
| 6,210,347 B1 | 4/2001 | Forsell | |
| 6,348,056 B1 | 2/2002 | Bates et al. | |
| 6,427,089 B1 | 7/2002 | Knowlton | |
| 6,450,946 B1 | 9/2002 | Forsell | |
| 6,454,699 B1 | 9/2002 | Forsell | |
| 6,460,543 B1 | 10/2002 | Forsell | |
| 6,511,490 B2 | 1/2003 | Robert | |
| 6,540,789 B1 | 4/2003 | Silverman et al. | |
| 6,558,400 B2 | 5/2003 | Deem et al. | |
| 6,605,111 B2 * | 8/2003 | Bose et al. | 623/1.18 |
| 6,627,206 B2 | 9/2003 | Lloyd | |
| 6,656,194 B1 | 12/2003 | Gannoe et al. | |
| 6,669,721 B1 * | 12/2003 | Bose et al. | 623/1.15 |
| 6,675,809 B2 | 1/2004 | Stack et al. | |
| 6,676,674 B1 | 1/2004 | Dudai | |
| 6,733,512 B2 | 5/2004 | McGhan | |
| 6,740,121 B2 | 5/2004 | Geitz | |
| 6,746,460 B2 | 6/2004 | Gannoe et al. | |
| 6,755,869 B2 | 6/2004 | Geitz | |
| 6,802,868 B2 | 10/2004 | Silverman et al. | |
| 6,845,776 B2 | 1/2005 | Stack et al. | |
| 6,879,859 B1 | 4/2005 | Boveja | |
| 6,916,326 B2 | 7/2005 | Benchetrit | |
| 6,946,002 B2 | 9/2005 | Geitz | |
| 6,981,980 B2 | 1/2006 | Sampson et al. | |
| 6,994,715 B2 | 2/2006 | Gannoe et al. | |
| 7,033,373 B2 | 4/2006 | de la Torre et al. | |
| 7,033,384 B2 | 4/2006 | Gannoe et al. | |
| 7,037,344 B2 | 5/2006 | Kagan et al. | |
| 7,054,690 B2 | 5/2006 | Imran | |
| 7,056,305 B2 | 6/2006 | Garza Alvarez | |
| 7,066,945 B2 * | 6/2006 | Hashiba et al. | 606/191 |
| 7,090,699 B2 | 8/2006 | Geitz | |
| 7,097,665 B2 | 8/2006 | Stack et al. | |
| 7,112,186 B2 | 9/2006 | Shah | |
| 7,121,283 B2 | 10/2006 | Stack et al. | |
| 7,152,607 B2 | 12/2006 | Stack et al. | |
| 7,172,613 B2 | 2/2007 | Wazne | |
| 7,175,638 B2 | 2/2007 | Gannoe et al. | |
| 7,177,693 B2 | 2/2007 | Starkebaum | |
| 2001/0011543 A1 | 8/2001 | Forsell | |
| 2002/0188354 A1 | 12/2002 | Peghini | |
| 2003/0049325 A1 | 3/2003 | Suwelack et al. | |
| 2003/0109892 A1 | 6/2003 | Deem et al. | |
| 2003/0120265 A1 | 6/2003 | Deem et al. | |
| 2003/0158564 A1 | 8/2003 | Benchetrit | |
| 2003/0199989 A1 | 10/2003 | Stack et al. | |
| 2003/0199990 A1 | 10/2003 | Stack et al. | |
| 2003/0199991 A1 | 10/2003 | Stack et al. | |
| 2004/0019388 A1 | 1/2004 | Starkebaum | |
| 2004/0024386 A1 | 2/2004 | Deem et al. | |
| 2004/0039452 A1 | 2/2004 | Bessler | |
| 2004/0044353 A1 | 3/2004 | Gannoe | |
| 2004/0044354 A1 | 3/2004 | Gannoe et al. | |
| 2004/0049209 A1 | 3/2004 | Benchetrit | |
| 2004/0082963 A1 | 4/2004 | Gannoe et al. | |
| 2004/0092892 A1 | 5/2004 | Kagan et al. | |
| 2004/0092974 A1 | 5/2004 | Gannoe et al. | |
| 2004/0117031 A1 | 6/2004 | Stack et al. | |
| 2004/0122452 A1 | 6/2004 | Deem et al. | |
| 2004/0122453 A1 | 6/2004 | Deem et al. | |
| 2004/0122526 A1 | 6/2004 | Imran | |
| 2004/0138760 A1 | 7/2004 | Schurr | |
| 2004/0138761 A1 | 7/2004 | Stack et al. | |
| 2004/0143342 A1 | 7/2004 | Stack et al. | |
| 2004/0153106 A1 | 8/2004 | Dudai | |
| 2004/0158331 A1 | 8/2004 | Stack et al. | |
| 2004/0186503 A1 | 9/2004 | DeLegge | |
| 2004/0220682 A1 | 11/2004 | Levine et al. | |
| 2004/0243152 A1 | 12/2004 | Taylor et al. | |
| 2005/0049718 A1 | 3/2005 | Dann et al. | |
| 2005/0070921 A1 | 3/2005 | Ortiz et al. | |
| 2005/0096750 A1 | 5/2005 | Kagan et al. | |
| 2005/0149141 A1 | 7/2005 | Starkebaum | |
| 2005/0149142 A1 | 7/2005 | Starkebaum | |
| 2005/0177181 A1 | 8/2005 | Kagan et al. | |
| 2005/0192531 A1 | 9/2005 | Birk | |
| 2005/0192614 A1 | 9/2005 | Binmoeller | |
| 2005/0209653 A1 | 9/2005 | Herbert et al. | |
| 2005/0222637 A1 | 10/2005 | Chen | |
| 2005/0222638 A1 | 10/2005 | Foley et al. | |
| 2005/0240239 A1 | 10/2005 | Boveja et al. | |
| 2005/0240279 A1 | 10/2005 | Kagan et al. | |
| 2005/0245957 A1 | 11/2005 | Starkebaum et al. | |
| 2005/0246037 A1 | 11/2005 | Starkebaum | |
| 2005/0250979 A1 | 11/2005 | Coe | |
| 2005/0256587 A1 | 11/2005 | Egan | |
| 2005/0267405 A1 | 12/2005 | Shah | |
| 2006/0015151 A1 | 1/2006 | Aldrich | |
| 2006/0020247 A1 | 1/2006 | Kagan et al. | |
| 2006/0030949 A1 | 2/2006 | Geitz | |
| 2006/0074450 A1 | 4/2006 | Boveja et al. | |
| 2006/0079944 A1 | 4/2006 | Imran | |
| 2006/0089571 A1 | 4/2006 | Gertner | |
| 2006/0129027 A1 | 6/2006 | Catona | |
| 2006/0129094 A1 | 6/2006 | Shah | |
| 2006/0161172 A1 | 7/2006 | Levine et al. | |
| 2006/0206063 A1 | 9/2006 | Kagan et al. | |
| 2006/0206064 A1 | 9/2006 | Kagan et al. | |
| 2006/0206160 A1 | 9/2006 | Cigaina et al. | |
| 2006/0249165 A1 | 11/2006 | Silverman et al. | |
| 2006/0253142 A1 | 11/2006 | Bjerken | |
| 2006/0257444 A1 | 11/2006 | Tropsha et al. | |
| 2006/0257445 A1 | 11/2006 | Tropsha et al. | |
| 2006/0257446 A1 | 11/2006 | Tropsha et al. | |
| 2006/0282107 A1 * | 12/2006 | Hashiba et al. | 606/153 |
| 2006/0293742 A1 | 12/2006 | Dann et al. | |
| 2007/0004963 A1 | 1/2007 | Benchetrit | |
| 2007/0010794 A1 | 1/2007 | Dann et al. | |
| 2007/0010864 A1 | 1/2007 | Dann et al. | |
| 2007/0010865 A1 | 1/2007 | Dann et al. | |
| 2007/0010866 A1 | 1/2007 | Dann et al. | |
| 2007/0021761 A1 | 1/2007 | Phillips | |
| 2007/0038308 A1 * | 2/2007 | Geitz | 623/23.65 |
| 2007/0239284 A1 * | 10/2007 | Skerven et al. | 623/23.65 |

FOREIGN PATENT DOCUMENTS

| | | |
|---|---|---|
| EP | 1520531 A1 | 4/2005 |
| WO | WO 01/10290 A2 | 2/2001 |
| WO | WO 2007/136468 A2 | 11/2007 |

* cited by examiner

METHOD OF DELIVERING AN INTRAGASTRIC DEVICE FOR TREATING OBESITY

TECHNICAL FIELD

This invention relates to medical devices, and more particularly to obesity treatment devices that can be placed in the stomach of a patient to occupy volume in the gastric lumen.

BACKGROUND OF THE INVENTION

It is well known that obesity is a very difficult condition to treat. Methods of treatment are varied, and include drugs, behavior therapy, and physical exercise, or often a combinational approach involving two or more of these methods. Unfortunately, results are seldom long term, with many patients eventually returning to their original weight over time. For that reason, obesity, particularly morbid obesity, is often considered an incurable condition. More invasive approaches have been available which have yielded good results in many patients. These include surgical options such as bypass operations or gastroplasty. However, these procedures carry high risks, and are therefore not appropriate for most patients.

In the early 1980s, physicians began to experiment with the placement of intragastric balloons to reduce the size of the stomach reservoir, and consequently its capacity for food. Once deployed in the stomach, the balloon helps to trigger a sensation of fullness and a decreased feeling of hunger. These balloons are typically cylindrical or pear-shaped, generally range in size from 200-500 ml or more, are made of an elastomer such as silicone, polyurethane, or latex, and are filled with air, water, or saline. While some studies demonstrated modest weight loss, the effects of these balloons often diminished after three or four weeks, possibly due to the gradual distension of the stomach or the fact that the body adjusted to the presence of the balloon. Other balloons include a tube exiting the nasal passage that allows the balloon to be periodically deflated and re-insufflated to better simulate normal food intake. However, the disadvantages of having an inflation tube exiting the nose are obvious.

The experience with balloons as a method of treating obesity has provided uncertain results, and has been frequently disappointing. Some trials failed to show significant weight loss over a placebo, or were ineffective unless the balloon placement procedure was combined with a low-calorie diet. Complications have also been observed, such as gastric ulcers, especially with use of fluid-filled balloons, and small bowel obstructions caused by deflated balloons. In addition, there have been documented instances of the balloon blocking off or lodging in the opening to the duodenum, wherein the balloon may act like a ball valve to prevent the stomach contents from emptying into the intestines.

Unrelated to the above-discussed methods for treating obesity, it has been observed that the ingestion of certain indigestible matter, such as fibers, hair, fuzzy materials, etc., can collect in the stomach over time, and eventually form a mass called a bezoar. In some patients, particularly children and the mentally handicapped, bezoars often result from the ingestion of plastic or synthetic materials. In many cases, bezoars can cause indigestion, stomach upset, or vomiting, especially if allowed to grow sufficiently large. It has also been documented that certain individuals having bezoars are subject to weight loss, presumably due to the decrease in the size of the stomach reservoir. Although bezoars may be removed endoscopically, especially in conjunction with a device known as a bezotome or bezotriptor, they, particularly larger ones, often require surgery.

What is needed is method of delivering an intragastric device that provides the potential weight loss benefits of a bezoar or intragastric balloon without the associated complications. Ideally, such a-method should be well-tolerated by the patient, effective over a long period of time, and easy to place and retrieve.

SUMMARY OF THE INVENTION

These and other advantages, as well as the invention itself, will become apparent in the details of construction and operation as more fully described below. Moreover, it should be appreciated that several aspects of the invention can be used with other types of intragastric devices or procedures used for the treatment of obesity.

In a first aspect, an intragastric member is provided. The intragastric member comprises a tubular sheet of material that is partitioned into a first bundle and a second bundle by a first retaining member and a second retaining member. The second retaining member is disposed distal of the first retaining member, and the first and second bundles extend circumferentially to form a lumen. A first suture tie and a second suture tie are provided. The first suture tie comprises a first proximal end and a first distal end. The first proximal end is a first free end that extends within the lumen and the first distal end is affixed to the first retaining member. The second suture tie comprises a second proximal end and a second distal end. The second proximal end is a second free end that extends within the lumen and the second distal end is affixed to the second retaining member. The first suture tie comprises a first ratcheted element and the second suture tie comprises a second ratcheted element, the first and the second ratcheted elements adapted to maintain the first and the second bundles in a compressed configuration.

In a second aspect, an intragastric device for the treatment of obesity is provided. A delivery tube comprising a proximal end, a distal end, and a lumen extends therebetween. An intragastric member is provided comprising a tubular sheet of material. The intragastric member is partitioned into a first bundle and a second bundle by a first retaining member and a second retaining member disposed distal of the first retaining member, the first and the second bundles being slidably disposed along the delivery tube and extending circumferentially about the delivery tube. A first suture tie and a second suture tie are provided. The first suture tie comprises a first proximal end and a first distal end, the first proximal end being a first free end that extends within the lumen of the delivery tube and the first distal end affixed to the first retaining member. The second suture tie comprises a second proximal end and a second distal end, the second proximal end being a second free end that extends within the lumen of the delivery tube and the second distal end affixed to the second retaining member.

In a third aspect, a method of treatment of obesity in mammals is provided. An intragastric member is provided comprising a tubular sheet of material. The intragastric member is secured onto a delivery tube with a retaining member. The retaining member extends circumferentially about the intragastric member to partition the intragastric member into a first and a second bundle, the second bundle positioned proximal of the first bundle. The retaining member is secured with a suture tie comprising a proximal and a distal end, the proximal end being a free end that extends within a lumen and the distal end affixed to the retaining member. The proximal end of the suture tie is pulled in a proximal direction through the lumen such that the first and the second bundles advance distally along the delivery tube.

BRIEF DESCRIPTION OF SEVERAL VIEWS OF THE DRAWINGS

Several embodiments of the present invention will now be described by way of example with reference to the accompanying drawings, in which.

DETAILED DESCRIPTION OF THE INVENTION

Figure 1:
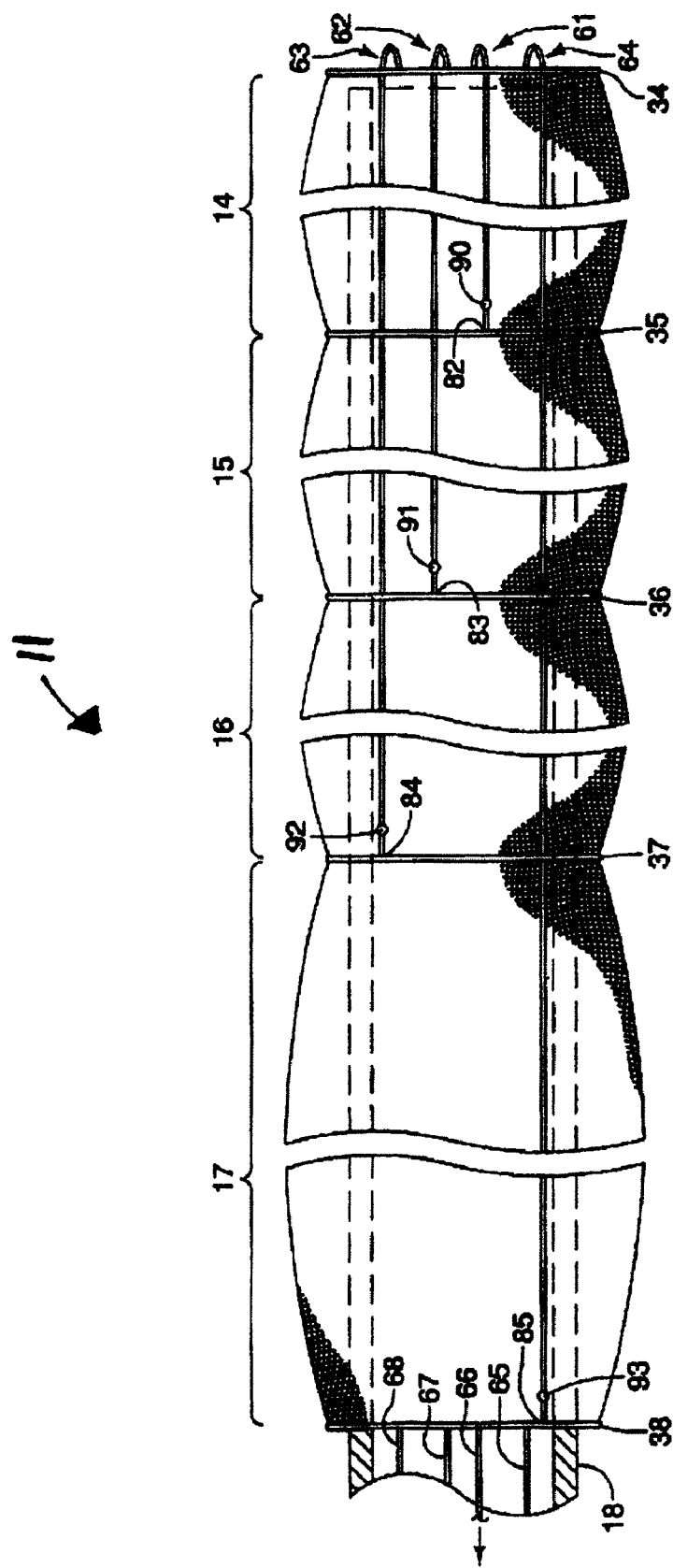
FIG. 1 is a side view of an intragastric member partitioned into bundles and disposed onto a delivery tube.
Figure 10:
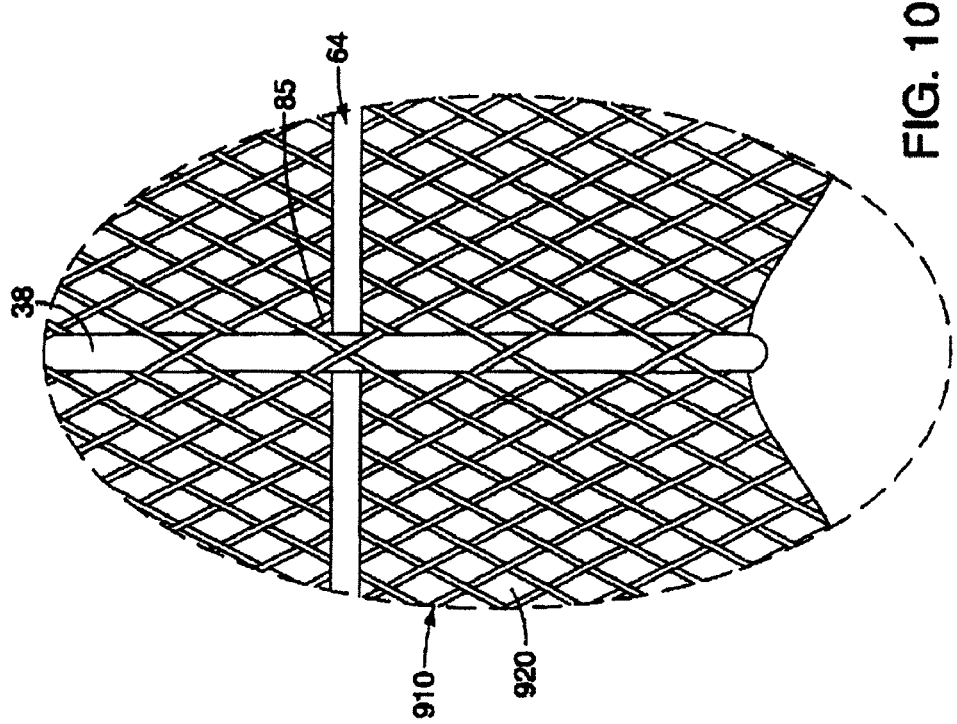
FIG. 10 shows each of the bundles removed from the delivery tube and cinched by ratcheting elements.
Figure 11:
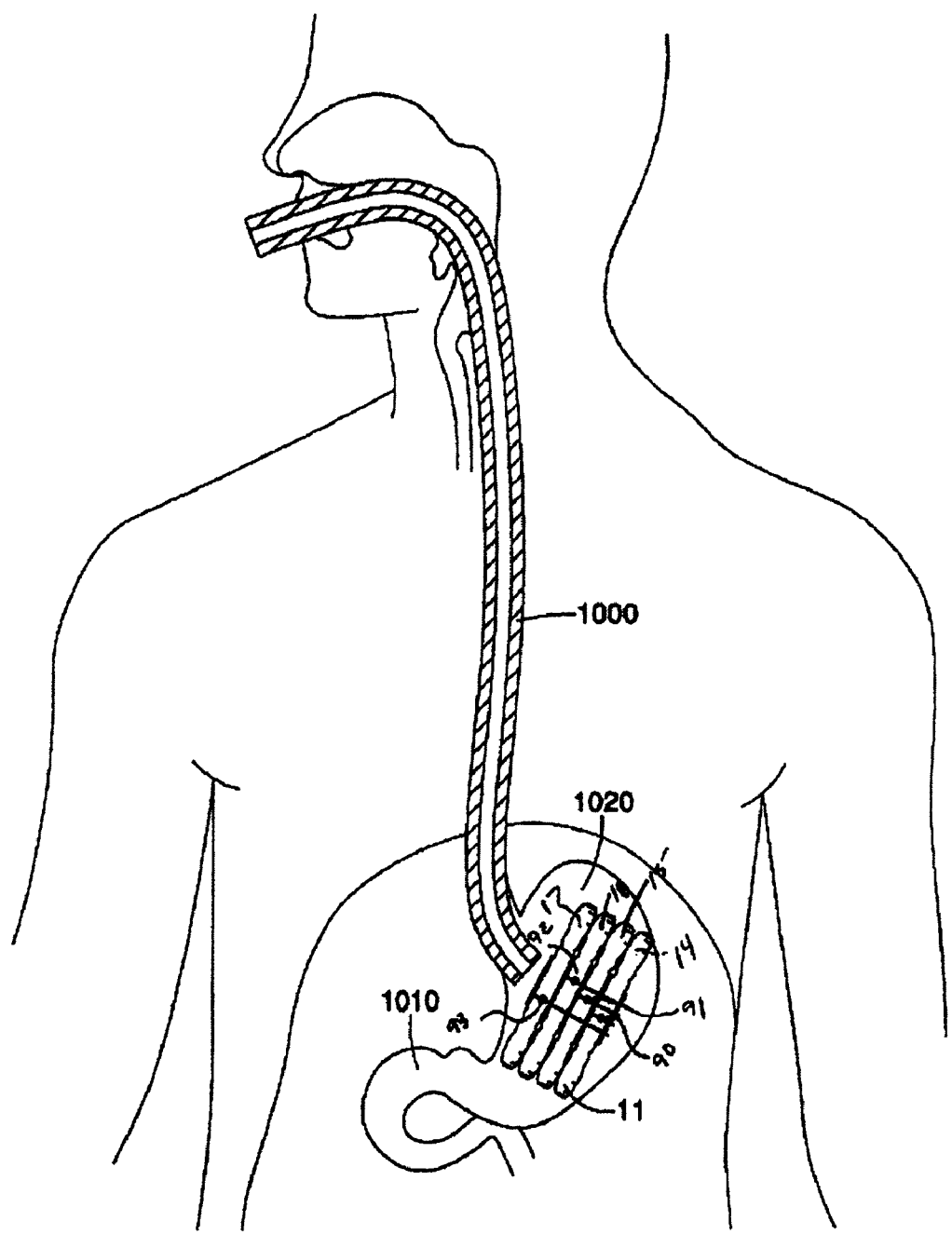
FIG. 11 shows the intragastric member fully deployed in the gastric lumen.

The obesity treatment apparatus depicted in FIGS. 1-11 comprises an intragastric member 11. The intragastric member 11 is preferably a high surface area mesh material (e.g., expandable polyethylene mesh), as shown in FIGS. 1 and 10 that is designed to displace volume within the gastric lumen. The implanted intragastric member 11 occupies a sufficient volume within the gastric lumen such that it does not pass through the pylorus 1010, as shown in FIG. 11. The exact volume required is patient specific, depending on the volume of the patient's gastric lumen. In one example, the apparent volume of the intragastric member 11 may range from about 500 mL to about 1500 mL. The term "apparent volume" as used herein refers to the volume of the intragastric member 11 prior to deployment into the gastric lumen.

As will be discussed with reference to FIGS. 1-11, delivery of the intragastric member 11 is enabled by partitioning the intragastric member 11 into a plurality of discrete bundles with retaining members that are circumferentially disposed along the longitudinal length of the intragastric member 11. Generally speaking, formation of the intragastric member 11 into bundles facilitates controlled delivery into the gastric lumen. The use of pull strings or suture ties enables deployment of the intragastric member 11 into the gastric lumen. The distal ends of the suture ties are affixed to the bundles. Pulling on the proximal free end of each of the suture ties enables the corresponding bundles to be advanced distally along a delivery tube. The suture ties are pulled until each of the bundles slide off from the delivery tube and enter into the gastric lumen.

FIG. 1 shows an exemplary intragastric member 11 that has been partitioned into a plurality of discrete bundles. Although the intragastric member 11 may comprise a relatively large number of bundles, for purposes of simplicity and clarity, only four bundles are shown. In particular, bundles 14, 15, 16, 17 are shown extending along the distal portion of the intragastric member 11. Compartmentalizing the intragastric member 11 into discrete bundles 14-17 facilitates its delivery and deployment into the gastric lumen. Retaining members 34, 35, 36, 37, 38 are circumferentially disposed at predetermined longitudinal lengths of the intragastric member 11 to form the bundles 14-17. The longitudinal length of each bundle 14, 15, 16, and 17 may vary and is partially dependent upon the degree of compartmentalization required. The shorter the longitudinal length of each of the bundles 14-17, the greater the ease of control may be in maneuvering the intragastric member 11 during delivery and deployment.

Retaining member 35 partitions the distal end of the intragastric member 11 into bundle 14 and bundle 15. Retaining member 36 further partitions the distal end of the intragastric member 11 into bundle 16, and retaining member 37 further partitions the intragastric member 11 into bundle 17. Additional retaining members 34 and 38, as shown in FIG. 1, may be provided to further constrain the intragastric member 11 into a low profile during delivery by substantially preventing the ends of bundle 14 and bundle 17 from undesirably flaring outwards and freely moving relative to delivery tube 18.

The intragastric member 11 with retaining members 34-38 are shown mounted over a delivery tube 18. FIG. 1 shows that the bundles 14-17 are constrained about delivery tube 18 at discrete intervals. Such constrainment of the bundles 14-17 enables a controlled delivery and deployment of the intragastric member 11 into a gastric lumen.

The retaining members 34-38 may be elastic bands or other structures, such as elastic rings. The retaining members 34-38 are secured to the intragastric member 11 and are not substantially moveable relative to each other. The attachment of the retaining members 34-38 to the intragastric member 11 at discrete locations enables the overall member 11 to achieve a low profile capable of being delivered to the gastric lumen. The retaining members 34-38 extend circumferentially about the intragastric member 11, as shown in FIG. 1. Each of the retaining members 34-38 is attached to its respective distal end of the suture tie that it contacts. As an example, FIG. 10 shows retaining member 38 attached by an adhesive to suture tie 64 at the distal end 85 of suture tie 64. The attachment of retaining member 38 to the distal end 85 of the suture tie 64 is sufficient so as to enable distal movement of both retaining member 38 and distal end 85 of suture tie 64 when the proximal end 65 of suture tie 64 is pulled. Other means of securing the retaining member 38 to the distal end 85 of suture tie 64 are contemplated. For example, the distal end 85 of suture tie 64 may be knotted to retaining member 38. Alternatively, the suture tie 64 may be riveted or crimped to the retaining member 38. For enhanced securement of the suture tie 64 to the bundles of the mesh 910 and retaining member 38, the suture tie 64 may also be interwoven through the interstices 920 of the mesh 910.

In the illustrative embodiments, the retaining members 34-38 (see FIG. 1) extend circumferentially about an intragastric member 11 to secure it onto a delivery tube 18. The retaining members 34-38 may be spaced apart from about 10 cm to about 30 cm to partition the intragastric member 11 into discrete bundle-like structures 14-17. Other spaced apart distances are contemplated.

Although five retaining members 34-38 are shown in FIG. 1, more than five or less than five retaining members may be used. The number of retaining members to be used is partially dependent upon the degree of partitioning of the intragastric member 11 that is desired during delivery. Generally speaking, a suitable number of retaining members should be disposed at a predetermined interval such that substantial portions of the intragastric member 11 are not free to radially and longitudinally move around during delivery. Such inadvertent movement increases the size of the member 11, thereby making delivery and deployment into the gastric lumen difficult.

Suture ties 61-64 are shown affixed to the bundles 14-17. The suture ties 61-64 are shown as pull strings which enable the bundles 14-17 to be advanced distally along the delivery tube 18 and ultimately to be released from the tube 18 into the gastric lumen. Suture tie 61 has a proximal end 66 and a distal end 82. The distal end of each suture tie as used herein refers to that portion of the suture tie that extends along the outer surface of the bundles 14-17. The proximal end of each suture tie as used herein refers to that portion of the suture tie that extends along the inner surface of the bundles 14-17 within the lumen 17 of the delivery tube 18. The distal end 82 is affixed to the retaining member 35, and the proximal end 66 is a free end that extends proximally within the lumen 18.

Suture tie 62 has a proximal end 67 and a distal end 83. The distal end 83 is attached to retaining member 36, and the proximal end 67 is a free end that extends proximally within the lumen 18. Note that the distal end 83 of the suture tie 62 also is attached to the retaining member 35.

Suture tie 63 has a proximal end 68 and a distal end 84. The distal end 84 is affixed to the retaining member 37, and the proximal end 68 is a free end that extends proximally within the lumen 18. Note that the distal end 84 of the suture tie 63 also is attached to retaining members 35 and 36.

Suture tie 64 has a proximal end 65 and a distal end 85. The distal end 85 is attached to the retaining member 38, and the proximal end 66 is a free end that extends proximally within the lumen 18. Note that the distal end 85 of the suture tie 64 extends proximally to the retaining members 35, 36, 37, and 38. Each of the free ends of the proximal ends 65-68 of the suture ties 61-64 extends proximally within the lumen 18 of the patient's esophagus and terminates out of the patient's mouth, thereby allowing a physician access to the suture ties 61-64 during deployment of the intragastric member 11.

The intragastric member 11 may be formed from a variety of materials. Preferably, the member 11 comprises a woven polymeric mesh, as shown in FIGS. 1-11. The mesh member 11 resembles a sock-like structure that is disposed about the delivery tube 18. The mesh sock-like structure is compliant and capable of being partitioned into bundles. The mesh sock-like structure is also flowable such that the individual bundles can be distally advanced along the delivery tube 18. In a preferred embodiment, the mesh 910 (FIG. 10) is formed from a low-density polyethylene having a thickness of about 40-50 microns. Details of a medical device formed from a mesh-like structure are described in U.S. patent application Ser. No. 11/743,732 which is incorporated herein by reference. Other types of materials are contemplated. For example, many well-known plastics such as polyesters, polyurethanes, polyethylenes, polyamides, and silicone may be used. Mammalian hair has been found to form natural bezoars, and thus, is also a possible material. Fluorinated ethylene propylene, ethylene vinyl acetate copolymer, nylon, or types of polymers that are biocompatible and to which food will generally not adhere may also be utilized.

Having described the structure of the intragastric member 11, a method of delivery and deployment of the intragastric member 11 will now be described. The intragastric member 11 is loaded onto a delivery tube 18 (FIG. 1). The intragastric member 11 may be configured to extend circumferentially about the delivery tube 18. The retaining members 34-38 are likewise disposed circumferentially about the intragastric member 11 at predetermined intervals to create the partition of bundles 14-17, as described above. The retaining members 34-38 also help secure the intragastric member 11 onto the delivery tube 18 in a constrained, low profile configuration. In the example shown in FIG. 1, the retaining members 34-38 may be spaced apart at about 30 cm increments along the distal end of the delivery tube 18.

Suture ties 61-64 may be attached longitudinally to the bundles 14-17 by interweaving the ties 61-64 through the interstices 920 of the mesh 910 (FIG. 10). The distal ends 82-85 of respective ties 61-64 may be disposed underneath the retaining members 34-38. Various other mechanisms for securing the intragastric member 11 to the delivery tube 18 are contemplated. For example, the sutures ties 61, 62, 63, 64 may be looped, sewn or threaded through the interstices 920 of the mesh 910 (FIG. 10). The proximal ends 65-68 are free ends that extend within the lumen 17 of the delivery tube 18, through the overtube 1000 (FIG. 10) and out of the patient's mouth for a physician to access during deployment of the bundles 14-17.

Having loaded the intragastric member 11 onto the delivery tube 11 with retaining members 34-38 and suture ties 61-64, delivery of the intragastric member 11 may begin. The intragastric member 11 and delivery tube 18 may be navigated through an overtube 1000 (FIG. 11) that spans along the patient's esophagus and into the entrance of the gastric lumen 1020 (FIG. 11). The delivery tube 18 may be navigated through the overtube 1000 and into the gastric lumen 1020 with the intragastric member 11 being configured in the constrained, low profile state by virtue of the bundles 14-17 (FIG. 1).

After the delivery tube 18 has been introduced into the gastric lumen 1020, deployment of the bundles 14-17 of the intragastric member 11 may begin by pulling on each of the proximal ends 65-68 of the suture ties 61-64 as will now be described. The proximal ends 65-68 may be color coded to help the operator identify which of the suture ties 61-64 is being pulled. Other means for logically identifying and organizing the proximal ends 61-64 are contemplated. For example, the proximal ends 61-64 may be wound so as to create a user-friendly configuration.

Figure 2:
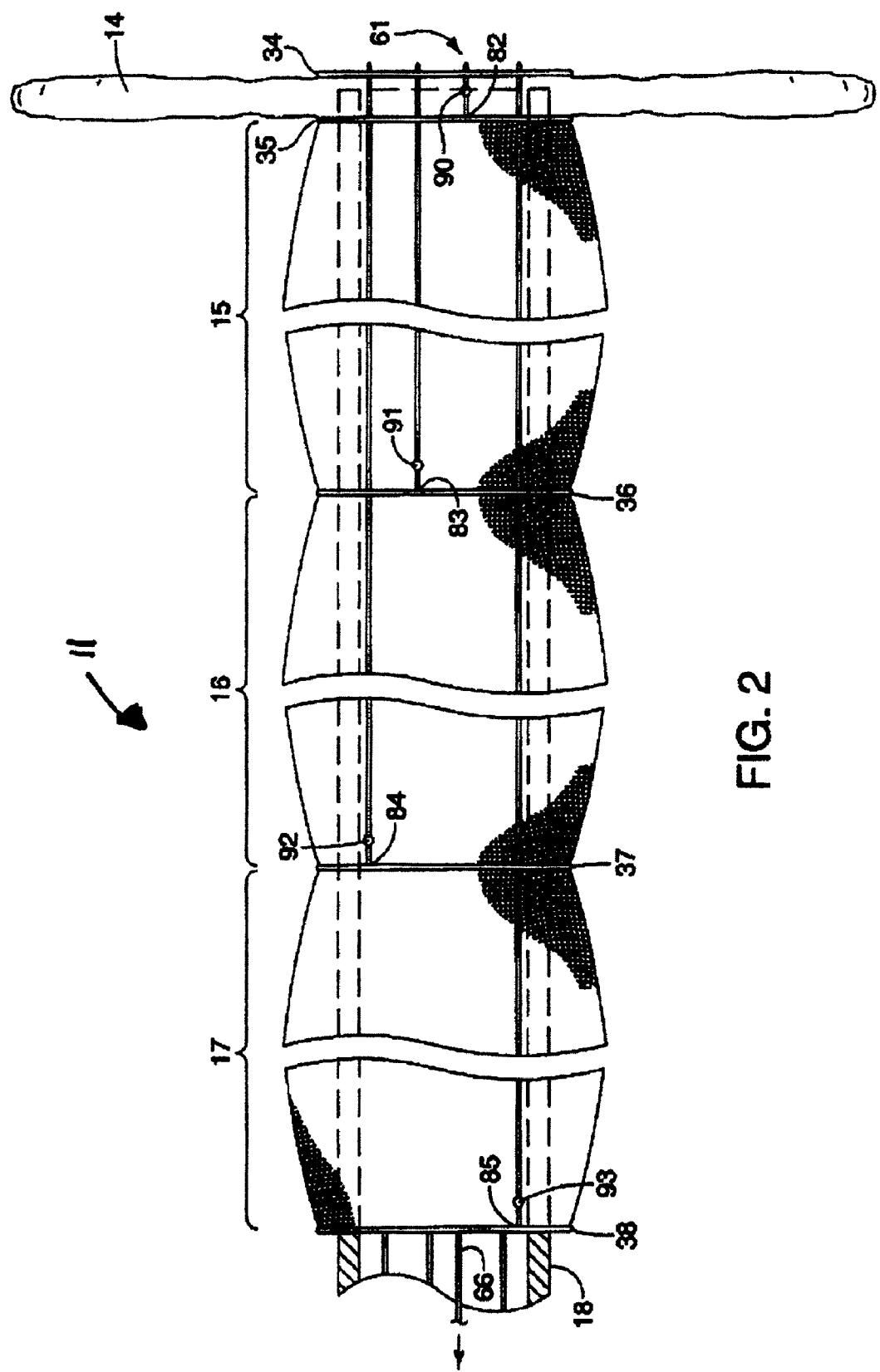
FIG. 2 is a side view of the delivery device of FIG. 1 in which the bundles have been advanced distally.

Proximal end 66 of suture tie 61 is pulled (as indicated by the arrow in FIG. 1) with a predetermined amount of force to cause the first bundle 14 to move toward the distal (forward) end of the delivery tube 18. Movement of the first bundle 14 towards the distal edge of the delivery tube 18 causes the first bundle 14 to become compressed, as shown in FIG. 2. FIG. 2 shows that the first bundle 14 has compressed, as indicated by the crease lines. The predetermined amount of force with which the proximal end 66 of suture tie 61 is pulled and the elasticity of retaining member 35 may help to maintain the first bundle 14 in a compressed configuration at the distal end of the delivery tube 18. The elasticity of retaining member 35 about the mesh 910 (FIG. 10) of intragastric member 11 provides sufficient frictional engagement of bundle 14 with the delivery tube 18 such that the bundle 14 does not readily slide off from the distal end of the delivery tube 18 at this juncture. Such frictional engagement may provide incremental and controlled deployment of each bundle 14-17 from the delivery tube 18. As the first bundle 14 shortens in length, the length of the distal end 82 of the suture tie 61 (i.e., the portion outside the tube 18) decreases while the length of the proximal end 66 of the suture tie 61 (i.e., the portion within the tube 18) proportionately increases.

Figure 3:
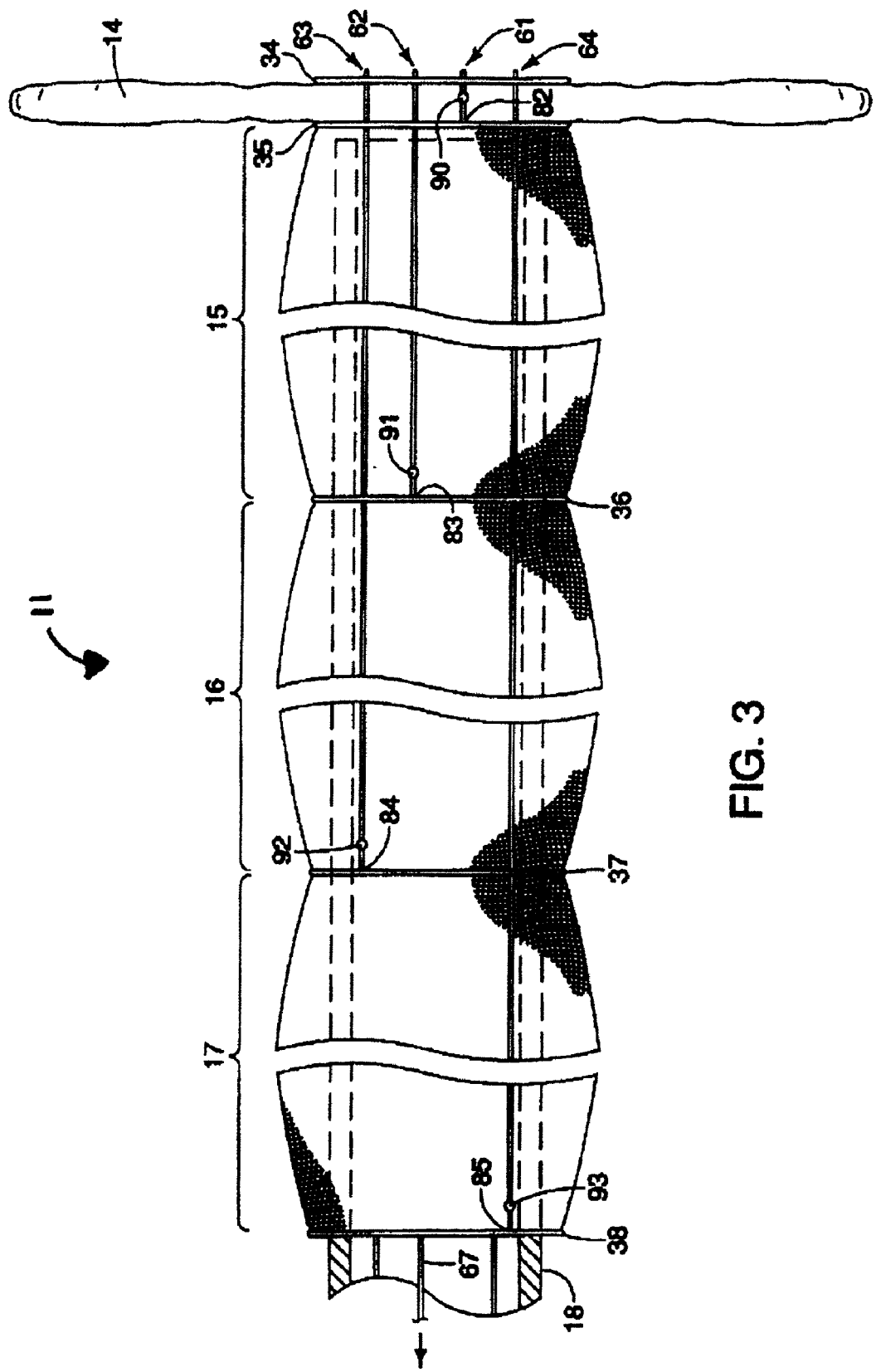
FIG. 3 is a side view of the delivery device of FIG. 1 in which the first bundle has been deployed into the gastric lumen.
Figure 4:
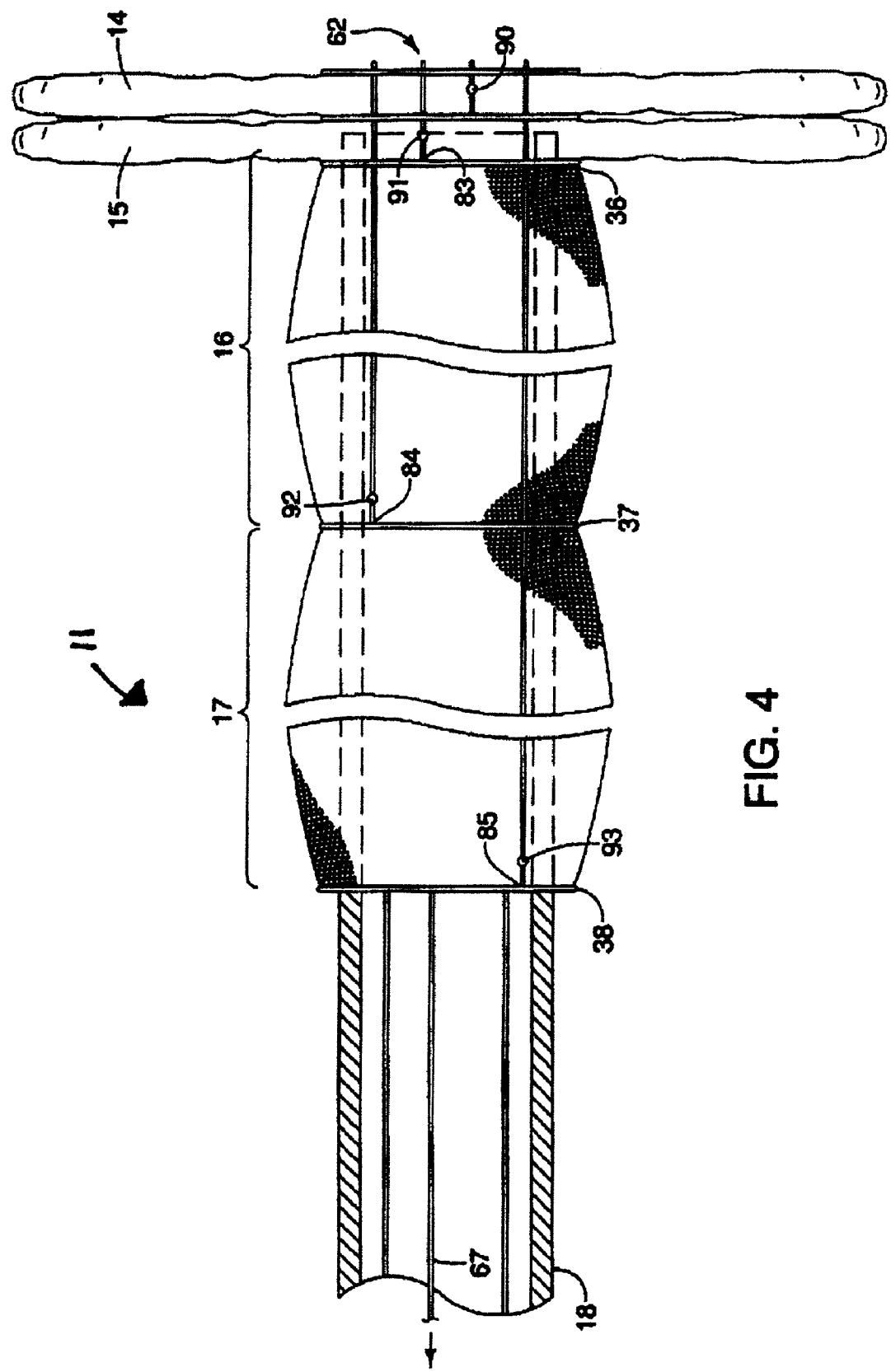
FIG. 4 is a side view of the delivery device of FIG. 1 in which each of the three bundles have advanced distally.

Further pulling of the suture tie 61 at its proximal end 66 (FIG. 2) with an appropriate amount of force causes the first bundle 14 to slide off from the distal end of the delivery tube 18 (FIG. 3) thereby leaving bundles 15-17 disposed along the delivery tube 18 as shown in FIG. 3. FIG. 3 shows that bundle 15 is the next bundle that will be removed from the delivery tube 18. Proximal end 67 of suture tie 62 is pulled (as indicated by the arrow in FIG. 3) with a predetermined amount of force to cause bundle 15 to move toward the distal edge of the delivery tube 18. Movement of the bundle 15 towards the distal edge of the delivery tube 18 causes the bundle 15 to become compressed, as shown in FIG. 4. Bundle 15 has compressed, as indicated by the crease lines. The predetermined amount of force with which the proximal end 67 of suture tie 62 is pulled and the elasticity of retaining member 36 may help to maintain the second bundle 15 in a compressed configuration at the distal end of the delivery tube 18. The elasticity of retaining member 36 about the mesh 910 (FIG. 10) of intragastric member 11 provides sufficient frictional engagement of the second bundle 15 with the delivery tube 18 such that the second bundle 15 does not readily slide off from the distal end of the delivery tube 18 at this juncture. As the bundle 15 has shortened in length, the length of the distal end 83 of the suture tie 62 (i.e., the portion outside the tube 18) has decreased while the length of the proximal end 67 of the suture tie 62 (i.e., the portion inside the tube 18) has proportionately increased.

Figure 5:
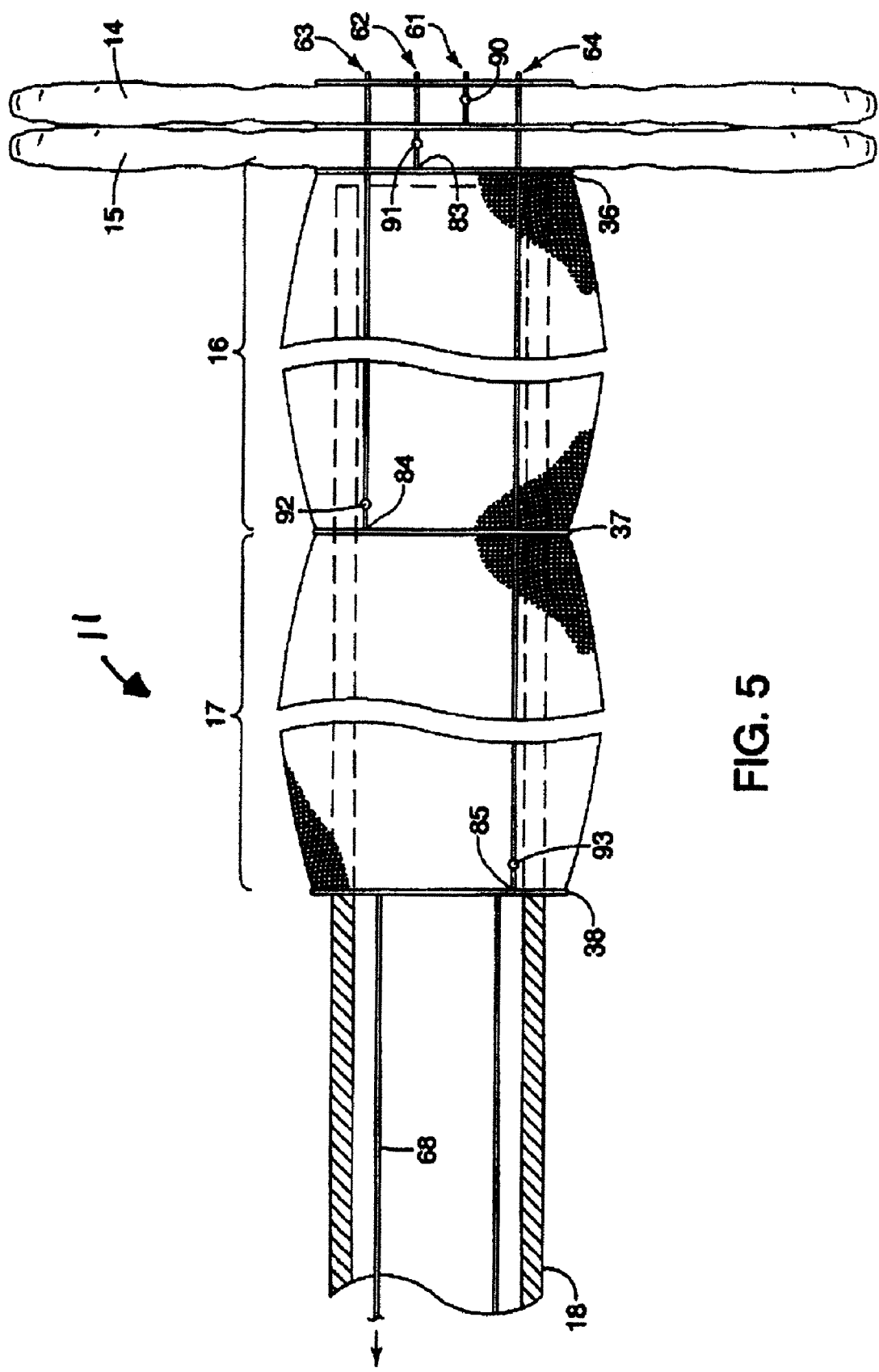
FIG. 5 is a side view of the delivery device of FIG. 1 in which the second bundle has been deployed into the gastric lumen.
Figure 6:
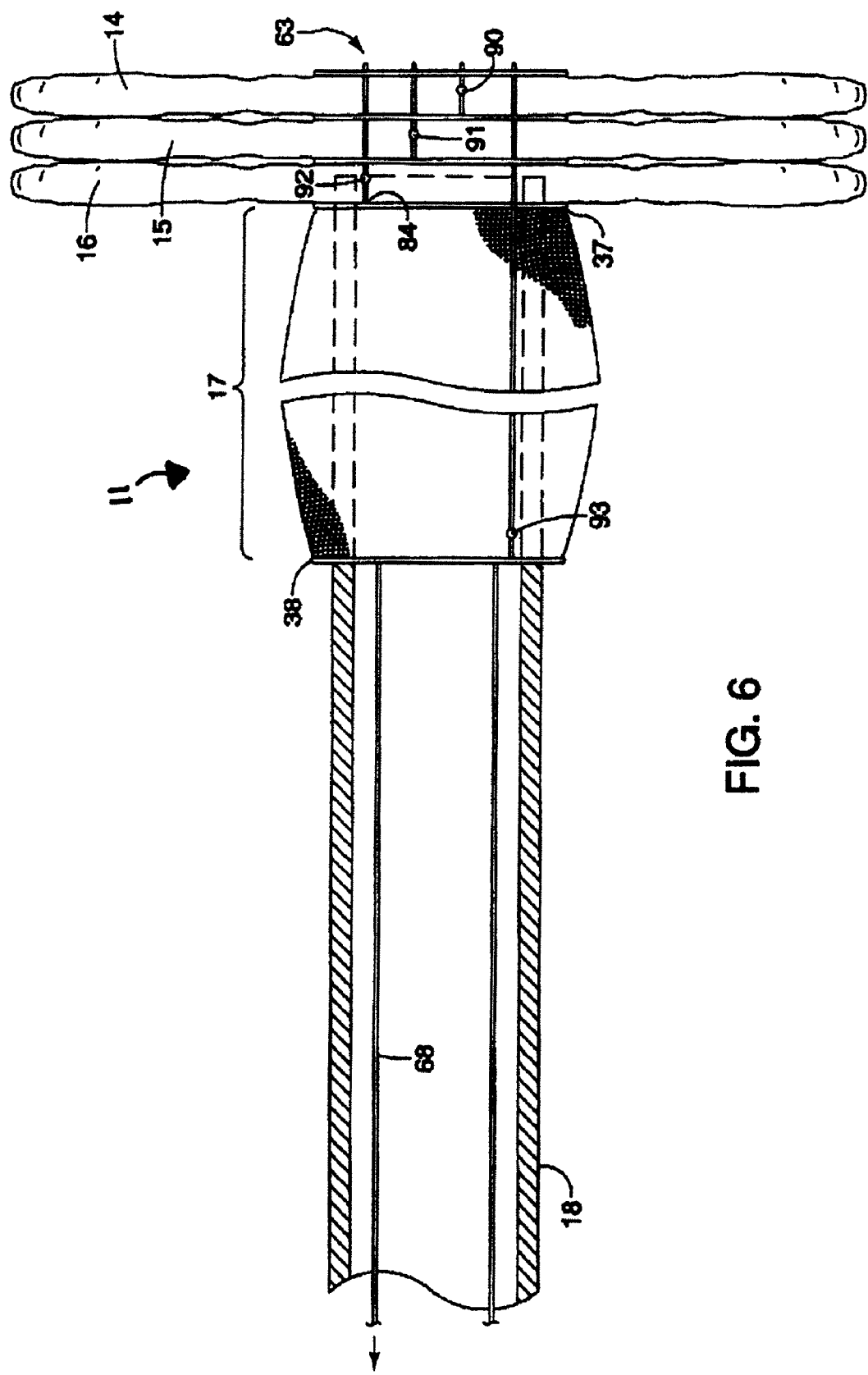
FIG. 6 is a side view of the delivery device of FIG. 1 in which each of the two bundles have been advanced distally.

Further pulling of the suture tie 62 at its proximal end 67 with a predetermined amount of force causes the bundle 15 to slide off from the distal end of the delivery tube 18 (FIG. 4), thereby leaving bundles 16 and 17 disposed along the delivery tube 18, as shown in FIG. 5. FIG. 5 shows that bundle 16 is the next bundle that will be removed from the delivery tube 18. Proximal end 68 of suture tie 63 is pulled (as indicated by the arrow in FIG. 5) with a predetermined amount of force causing bundle 16 to become compressed, as shown in FIG. 6. FIG. 6 shows that the bundle 16 has compressed, as indicated by the crease lines. The predetermined amount of force with which the proximal end 68 of suture tie 63 is pulled and the elasticity of retaining member 37 may help to maintain the third bundle 16 in a compressed configuration at the distal end of the delivery tube 18. The elasticity of retaining member 37 about the mesh 910 (FIG. 10) of intragastric member 11 provides sufficient frictional engagement of bundle 16 with the delivery tube 18 such that the bundle 16 does not readily slide off from the distal end of the delivery tube 18 at this juncture. As the bundle 16 has shortened in length, the length of the distal end 84 of the suture tie 63 (i.e., the portion outside the tube 18) has decreased while the length of the proximal end 68 of the suture tie 63 (i.e., the portion inside the tube 18) has proportionately increased.

Figure 7:
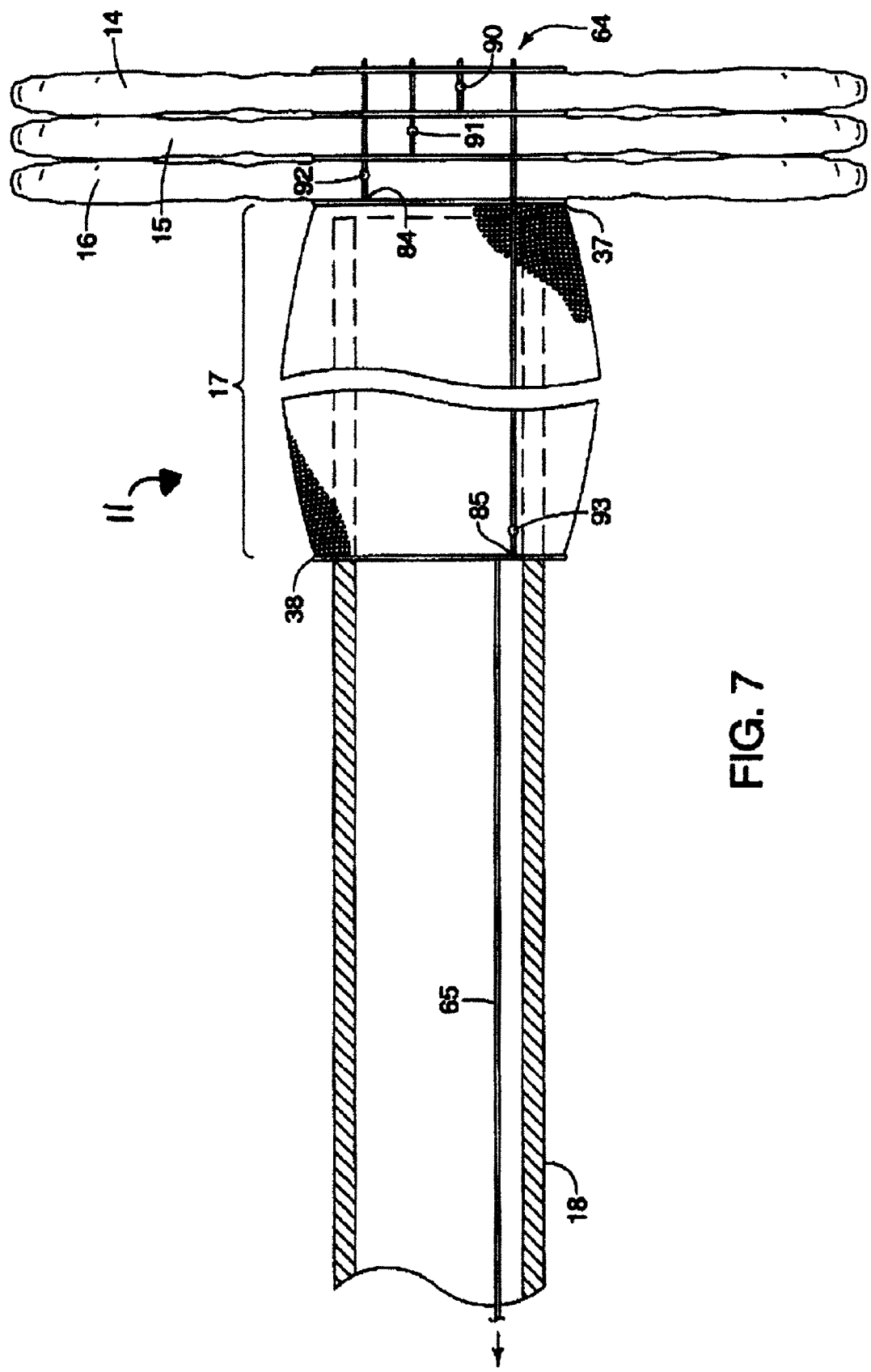
FIG. 7 is a side view of the delivery device of FIG. 1 in which the third bundle has been deployed into the gastric lumen.
Figure 8:
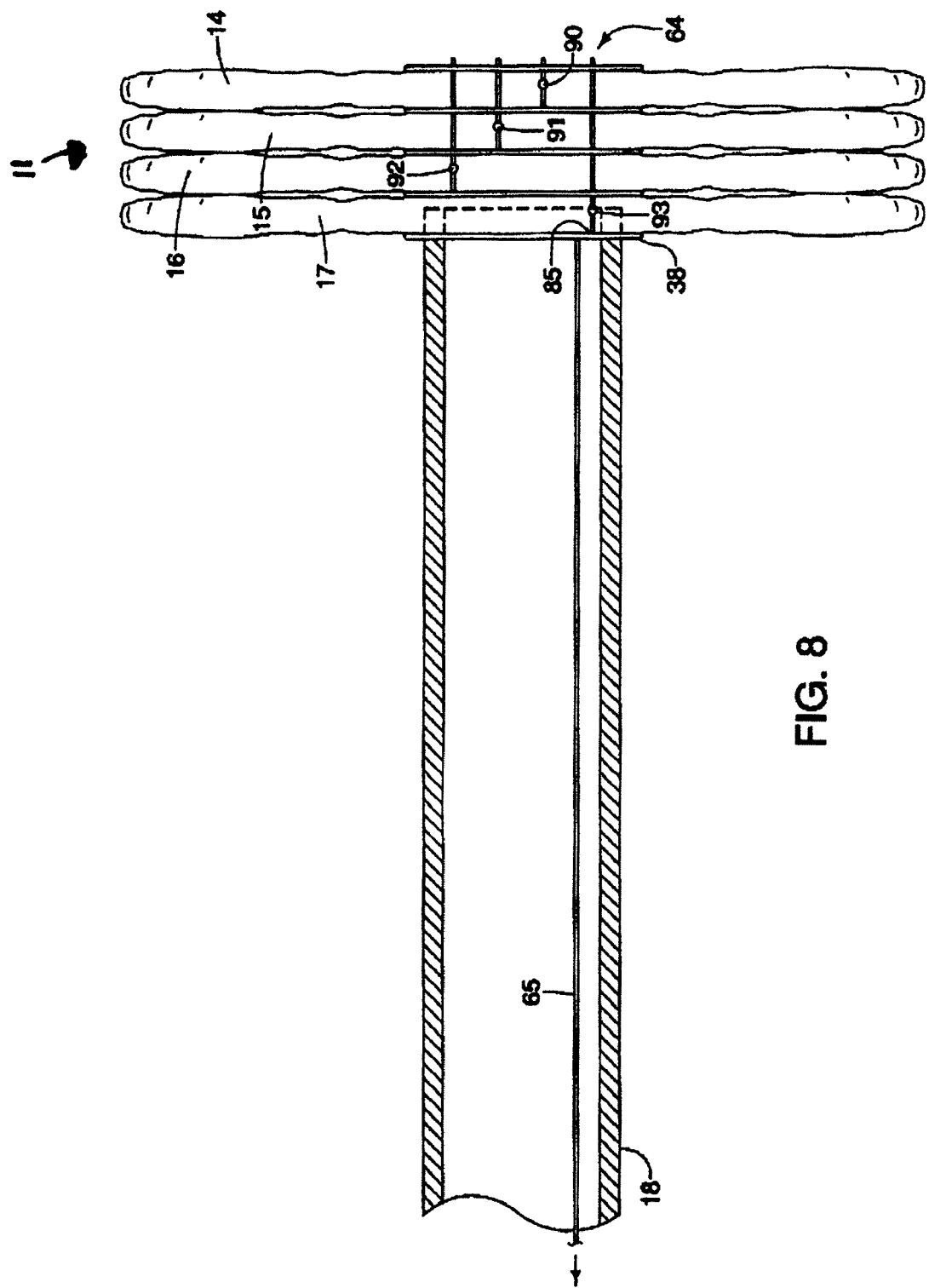
FIG. 8 is a side view of the delivery device of FIG. 1 in which the bundle has been advanced distally.

Further pulling of the suture tie 63 at its proximal end 68 (FIG. 6) causes the bundle 16 to slide off from the distal end of the delivery tube 18 (FIG. 7). At this juncture, bundle 17 is shown in FIG. 7 as the only remaining bundle 17 that is disposed along the delivery tube 18. Proximal end 65 of suture tie 64 is pulled (as indicated by the arrow in FIG. 7) causing the bundle 17 to become compressed, as shown in FIG. 8. FIG. 8 shows that the bundle 17 has compressed, as indicated by the crease lines. The predetermined amount of force with which the proximal end 65 of suture tie 64 is pulled and the elasticity of retaining member 38 may help to maintain the fourth bundle 17 in a compressed configuration at the distal end of the delivery tube 18. The elasticity of retaining member 38 about the mesh 910 (FIG. 10) of intragastric member 11 provides sufficient frictional engagement of bundle 17 with the delivery tube 18 such that the bundle 17 does not readily slide off from the distal end of the delivery tube 18 at this juncture. As the bundle 16 has shortened in length, the length of the distal end 85 of the suture tie 64 (i.e., the portion outside the tube 18) has decreased while the length of the proximal end 65 of the suture tie 64 (i.e., the portion inside the tube 18) has proportionately increased.

Figure 9:
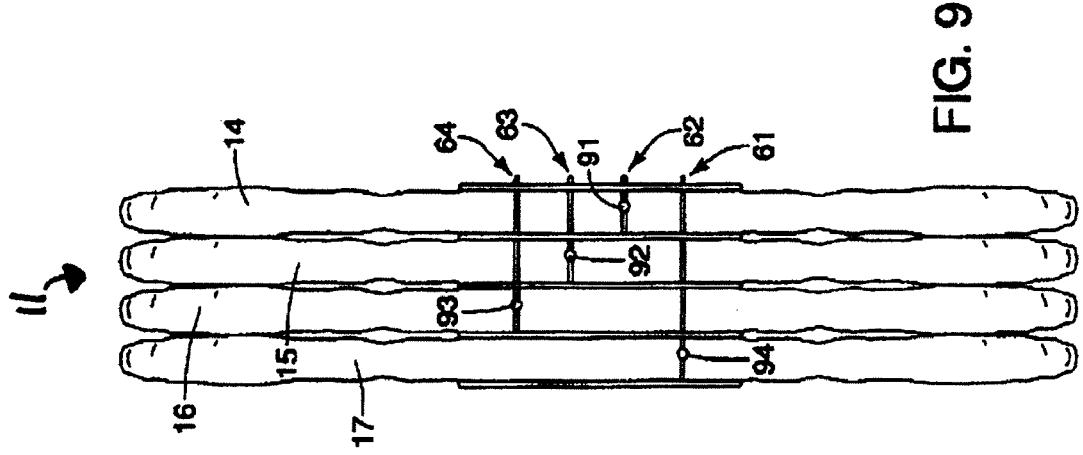
FIG. 9 is a blown up view of FIG. 1 of the intragastric member.

Further pulling of the suture tie 64 at its proximal end 65 (FIG. 8) causes the bundle 17 to slide off from the distal end of the delivery tube 18 (FIG. 9). At this juncture all of the bundles 14-17 are deployed in the gastric lumen 1020 (FIG. 11). The proximal ends 65-68 of each of the suture ties 61-64 may be severed and the delivery tube 18 may be removed through the overtube 1000 (FIG. 11).

FIG. 9 shows all of the bundles 14-17 deployed from the delivery tube 18. Beads 90-93 are shown affixed to the surface of their respective suture ties 61-64. The beads 90-93 serve as ratcheted structures which cinch their respective bundles 14-17 in the longitudinal direction and maintain the bundles 14-17 in a compressed and bundled configuration (FIG. 9). Other types of ratcheted structures to cinch the bundles 14-17 are contemplated and would be appreciated by one of ordinary skill in the art. For example, proximal and distal stoppers could be used to maintain the bundles 14-17 in a compressed configuration. Alternatively, all of the bundles 14-17 may be knotted or tied together.

The above described procedure of delivery may be repeated by loading additional intragastric members 11 over the delivery tube 18 and pushing these intragastric members 11 against the previously inserted bundles 14-17 until all of the bundles 14 have been inserted into the gastric lumen. Deployment of additional intragastric members 11 may occur if greater displacement of the gastric lumen is required.

As an alternative to the above-described procedure, suture tie 64 may be pulled to cause distal movement of bundle 17. Distal movement of bundle 17 may push against bundles 14-16 thereby causing them to also move distally such that bundles 14-17 attain a compressed configuration at the distal end of the delivery tube 18.

FIG. 11 show the completely deployed intragastric member 11 implanted in the gastric lumen 1020. The deployed intragastric member 11 is shown in an unconstrained state without any stoppers to constrain the bundles 14-17. The bundles 14-17 are in a compressed configuration yet occupy sufficient volume such that they do not exit through the pylorus 1010. Beads 90-93 cinch the bundles 14-17 and maintain the bundles 14-17 in a compressed configuration within the gastric lumen 1020.

The intragastric member 11 is sufficiently large such that it occupies a volume in the gastric lumen 1020 that prevents the bundles 14-17 from passing through the pylorus 1010. The intragastric member 11 occupies a sufficiently large volume in the gastric lumen 1020 to cause a patient to eat less and achieve satiety.

The above-described embodiments discuss a method for delivering a large volume of material into a gastric lumen in a controlled and incremental manner. Various sized intragastric bags may be delivered using the above embodiments. In one example, an intragastric bag having a starting longitudinal length of about four feet and a width of about six inches may be partitioned into four bundles, each of the four bundles having a longitudinal length of about one foot and a width of about one inch. More retaining members may be utilized to further partition the intragastric bag, thereby reducing the profile of the assembled bundles onto the delivery tube 18. After deployment into the gastric lumen, each of the bundles may have a width of about six inches and a longitudinal length of about one-and-a-half inches. Generally speaking, the width of the deployed bundles 14-17 is greater than the width of the bundles 14-17 assembled onto delivery tube 18.

To remove the intragastric member 11 from the gastric lumen 1020, the retaining members 34-38 are typically cut so as to enable the bundles 14-17 to uncompress and be withdrawn from the lumen 1020. One end of the member 11 is then grasped by forceps or similar device and pulled out of the patient.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. An intragastric device for the treatment of obesity, the intragastric device comprising:
   an intragastric member comprising a generally tubular sheet of material having a lumen extending there through, the intragastric member partitioned into a first bundle and a second bundle disposed proximal of the first bundle, the first and the second bundles formed by a first retaining member and a second retaining member, the first retaining member disposed between the first and second bundles, the second retaining member disposed proximal of the first retaining member and proximal of the second bundle, the first and second retaining members extending circumferentially about the lumen;
   a first suture tie and a second suture tie, the first suture tie comprising a first proximal end and a first distal end, the first proximal end being a first free end that extends within the lumen and the first distal end affixed to the first retaining member, the second suture tie comprising a second proximal end and a second distal end, the second proximal end being a second free end that extends within the lumen and the second distal end affixed to the second retaining member;
   wherein the intragastric member comprise a meshed sock-like structure, and the first and the second retaining members are interwoven about the mesh;
   wherein the first and second bundles are each movable from a longitudinally extended configuration to a longitudinally compressed configuration,
   wherein the first and second suture ties are configured to move the first and second bundles from the longitudinally extended configuration to the longitudinally compressed configuration, and
   wherein the first suture tie comprises a first ratcheted element and the second suture tie comprises a second ratcheted element, the first and the second ratcheted elements adapted to secure the first and the second bundles in the longitudinally compressed configuration.

2. The intragastric device according to claim 1, wherein the first and the second bundles are disposed onto a delivery tube, the delivery tube extending through the lumen of the intragastric member.

3. The intragastric device according to claim 2, wherein the first suture comprises a first proximal end portion that extends within the delivery tube and a first distal end portion that extends over the first bundle.

4. The intragastric device according to claim 1, wherein the intragastric member has an apparent volume ranging between about 500 mL to about 1500 mL.

5. The intragastric device according to claim 1, wherein the second suture tie comprises a second proximal end portion that extends within the delivery tube and a second distal end portion that extends over the second bundle.

6. The intragastric device according to claim 1, wherein the first and the second bundles are circumferentially constrained about a delivery tube at discrete intervals when in the longitudinally extended configuration and the that the first and second retainers are disposed about the delivery tube at spaced apart locations.

7. The intragastric device according to claim 1, wherein the first and second retainers are disposed adjacent to each other when the first and the second bundles are in the longitudinally compressed configuration.

8. An intragastric device for the treatment of obesity, the intragastric device comprising:
   an intragastric member comprising a generally tubular sheet of material having a lumen extending there through, the intragastric member partitioned into a first bundle and a second bundle disposed proximal of the first bundle, the first and the second bundles formed by a first retaining member and a second retaining member, the first retaining member disposed between the first and second bundles, the second retaining member disposed proximal of the first retaining member and proximal of the second bundle, the first and second retaining members extending circumferentially about the lumen;
   a first suture tie and a second suture tie, the first suture tie comprising a first proximal end and a first distal end, the first proximal end being a first free end that extends within the lumen and the first distal end affixed to the first retaining member, the second suture tie comprising a second proximal end and a second distal end, the second proximal end being a second free end that extends within the lumen and the second distal end affixed to the second retaining member;
   wherein the intragastric member comprise a meshed sock-like structure, and the first and the second suture ties are interwoven with the mesh;
   wherein the first and the second bundles are each movable from a longitudinally extended configuration to a longitudinally compressed configuration,
   wherein the first and second suture ties are configured to move the first and second bundles from the longitudinally extended configuration to the longitudinally compressed configuration, and
   wherein the first suture tie comprises a first ratcheted element and the second suture tie comprises a second ratcheted element, the first and the second ratcheted elements adapted to secure the first and the second bundles in the longitudinally compressed configuration.

9. The intragastric device according to claim 8, wherein the first and the second bundles are disposed onto a delivery tube, the delivery tube extending through the lumen of the intragastric member.

10. The intragastric device according to claim 9, wherein the first suture comprises a first proximal end portion that extends within the delivery tube and a first distal end portion that extends over the first bundle.

11. The intragastric device according to claim 8, wherein the intragastric member has an apparent volume ranging between about 500 mL to about 1500 mL.

12. The intragastric device according to claim 8, wherein the second suture tie comprises a second proximal end portion that extends within the delivery tube and a second distal end portion that extends over the second bundle.

13. The intragastric device according to claim 8, wherein the first and the second bundles are circumferentially constrained about a delivery tube at discrete intervals when in the longitudinally extended configuration and the that the first and second retainers are disposed about the delivery tube at spaced apart locations.

14. The intragastric device according to claim 8, wherein the first and second retainers are disposed adjacent to each other when the first and the second bundles are in the longitudinally compressed configuration.

* * * * *